Feb. 27, 1945. J. D. DAVIS Plant Pat. 651
PEACH TREE
Filed Sept. 18, 1944
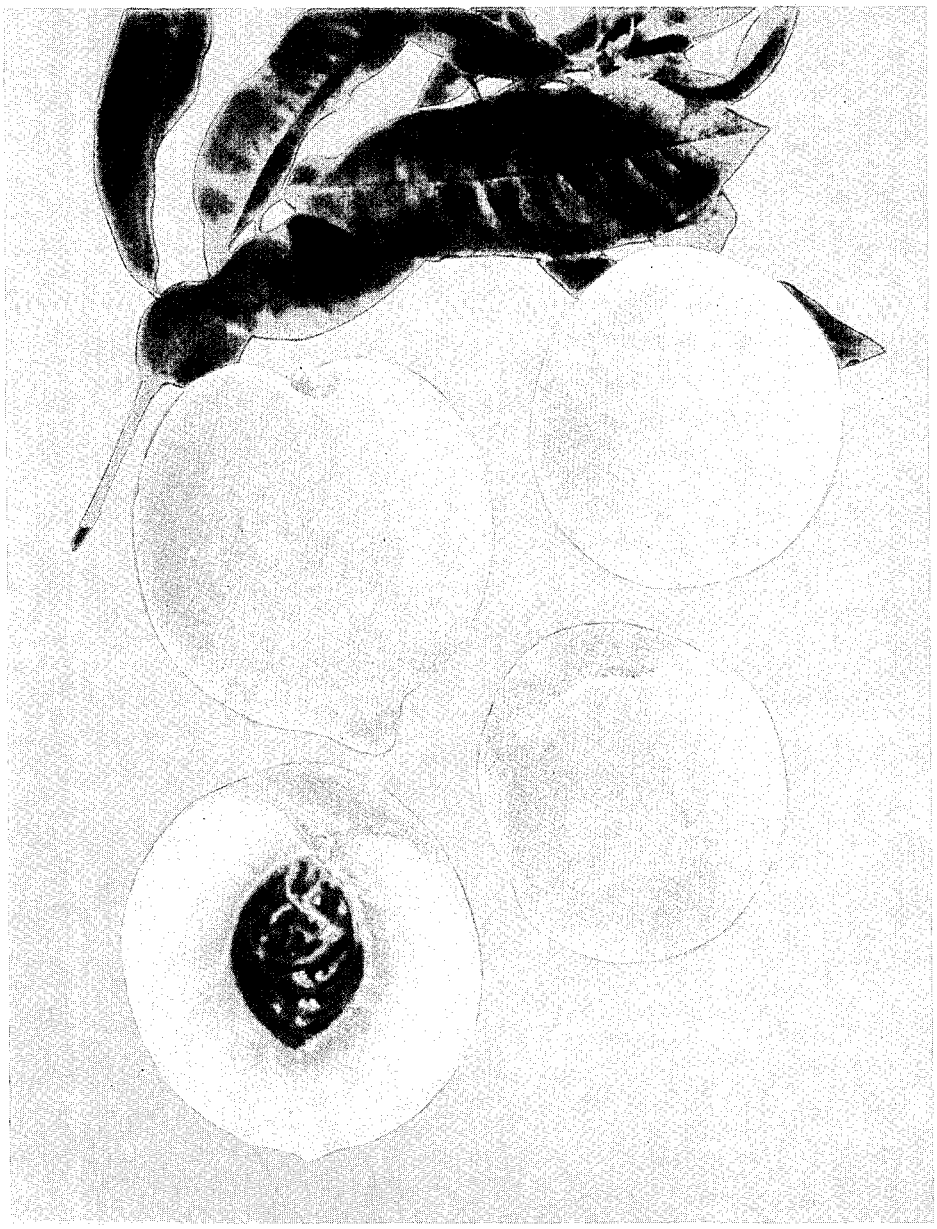
Inventor
J. D. Davis
By Lida Boyer
Administratrix of the estate of
J. D. Davis deceased
By Robb & Robb
Attorneys Patented Feb. 27, 1945

Plant Pat. 651

UNITED STATES PATENT OFFICE

651

PEACH TREE

John D. Davis, deceased, late of Long Beach, Calif., by Lida Boyer, administratrix, Long Beach, Calif., assignor to Armstrong Nurseries, Inc., Ontario, Calif., a corporation of California Application September 18, 1944, Serial No. 554,651

1 Claim. (Cl. 47—62)

This discovery relates to a new and distinct variety of peach tree, originating as a seedling and recognized as having superior attributes representing desirable improvements in the line of fruit producing trees.

Among the distinctive characteristics of this new variety, in the order of their importance, may be noted:

(*a*) The delectable flavor and juiciness of the fruit, as compared with other peach varieties ripening near its season, that is within two weeks earlier or later.

(*b*) Its low chilling requirement in combination with late ripening, when compared with other late-ripening peaches. To be more specific in connection with this point, this chilling requirement is about mid-way between that of the two well known California varieties, the "Babcock Freestone" and the "Sims Cling." The value of this distinguishing characteristic is most appreciated when it is understood that this low chilling requirement allows the variety to set a good crop of well-flavored fruit each year, where other late-ripening varieties often are without fruit following mild winters in southern California.

(*c*) Distinct difference as to size and shape—some globose and quite symmetrical, some depresso-globose, and others asymmetrical tending toward turbinate.

(*d*) Moderate toughness of the skin of the fruit and somewhat light color, as compared with many of the so-called yellow-fleshed peaches, and the extent of the area and intensity of the blush in pink and reddish tones, varying from peach to peach and depending apparently on the amount of sunlight which the fruit received.

(*e*) The orange-yellow color of the flesh, considerably deeper than most of the so-called yellow-fleshed peaches; and the considerable red color around the pit, which latter is somewhat above average size.

(*f*) Unusually shallow stem cavity and the accompanying characteristic of the fruit hanging on the tree very well after ripening, sometimes even until after starting to decompose.

(*g*) Average ripening season, from September 25 to October 10 (in southern California), said season varying with the mildness of the winter preceding the crop and being always late after a severe winter.

(*h*) Absence of tendency to oxidize (turn brown) to any extent after being cut, even after being exposed six to eight hours.

Asexual reproduction of the new variety shows the above characteristics to be established and fixed.

The following is a detail description of this new variety, according with observations of specimens grown at Ontario, California, color terminology thereof referring to Robert F. Wilson Horticultural Charts:

Tree: Medium size; vigorous; upright; spreading; open; vase formed; productive; regular bearer.

*Trunk.*—Medium stocky; medium smooth.

*Branches.*—Medium stocky; medium smooth; dull. *Lenticels*—medium number; small size.

*Leaves.*—Length, from 2" to 4¼"; width, from ¾" to 1½"; medium to small; lanceolate; cuneate toward base; acutely pointed; medium thick; smooth. Upper side of leaf, near Leek Green, Plate 000858, Chart II, page 197; under side, near Willow Green, Plate 000862/1, Chart II, page 199. *Margin*—glandular, from 110 to 130 marginal glands; finely serrate. *Petiole*—medium length; medium thick. *Petiolate glands*—Average number, from 1 to 4; alternate; medium size; mixed. Color—from near Fern Green, Plate 0862/1, Chart II, page 186, to near Garnet Brown, Plate 009818/1, Chart II, page 192, some deciduous. Position—on each side of petiole and encroaching on margin of leaf. Stipules—early deciduous.

*Flower buds.*—Half hardy; medium to small size; medium to short length; conic to pointed; plump; free.

*Flowers.*—Dates first and full bloom—March 18 and April 2, respectively, in 1943. Early compared with other varieties near same season of ripening; medium to small size; Pink.

Fruit: Maturity when described—eating ripe but firm; date, October 1, 1943. Dates first and last picking, September 20th–October 7th, (1943).

*Size.*—Variable; large to medium size. Diameter axial—2¼" to 3". Transverse in suture plane—2¼" to 2¾". At right angles to suture plane—2⅜" to 2⅞".

*Form.*—Variable; symmetrical to unsymmetrical; at times compressed transversely toward suture. Some fruits have a pronounced beak at the apical end, other fruits are almost completely round, except for the stem cavity, and still other fruits are intermediate between these two types, some of them having a pronounced lip on one side of the suture, and on others the lips are not pronounced.

*Suture.*—Line distinct; shallow to deep; extends from base to apex; has slight depression beyond pistil point at times. Sometimes this line does extend beyond apex to dorsal surface, and about ⅓ length of fruit.

*Ventral surface.*—Variably rounded. Lips, unequal when present. Ventral surface, some fruits do not show any lip whatever, others have a definite lip from center of fruit to apex.

*Stem cavity.*—Circular to elongated in suture plane with suture showing on one side. Depth, ⅝″ to ⅞″; breadth, ¾″ to 1½″; markings—at times pencilling (see skin color).

*Base.*—Rounded to truncate.

*Apex.*—Some fruits have little apex, or even a pistil point; while others have an elongated apex, and pistil point oblique.

*Stem.*—Length, about ¼″; medium stout; glabrous. Adherence to stone—strong to medium.

*Skin.*—Medium tender; slightly astringent; tenacious to flesh. Tendency to crack—none in dry season. When fruits were described, weather conditions were very dry; trees were irrigated, however. *Color*—blotches of color hues, near Uranium Green, Plate 63/2, Chart I, page 63, to near Chrome Yellow, Plate 605/1, Chart II, page 144, to Orange Buff, Plate 507/1, Chart II, page 133, and near Brick Red, Plate 016/2, Plate II, page 106. These often diffuse in stem cavity. *Down*—scant; short; does roll up when slightly rubbed.

*Flesh.*—Color—near Maize Yellow, Plate 607, Chart I, page 69. Surface of pit cavity—near Jasper Red, Plate 018, Chart II, page 107.

*Amygdalin.*—Scant; juice moderate, rich.

*Texture.*—Medium firm; fine; meaty.

*Fibres.*—Few; fine; tender.

*Ripens.*—Somewhat uneven; earliest at lip.

*Flavor.*—Subacid; mild; delicate.

*Aroma.*—Slight.

*Eating quality.*—Very good.

Stone: Free.

*Fibres.*—Short; parts from flesh smoothly.

*Size.*—Medium. Length, 1¼″ to 1⅝″; breadth, 1″; thickness, ¾″.

*Form.*—Oval; cuneate toward apex.

*Base.*—Straight; apex, acute.

*Sides.*—Some equal and some unequal; variable in shape. *Surface*—irregularly furrowed throughout; pitted throughout.

*Ridges.*—Uneven; rounded apex; jagged toward base.

*Pits.*—Elongated. Ventral edge—thin.

*Color of stone.*—Variable with ripeness of fruit and exposure to air and moisture.

*Tendency to split.*—None.

Use: Market or local; dessert.

Keeping quality: Good.

Resistant to: Delayed dormancy in southern California.

Shipping quality: Good.

What is claimed is:

A new and distinct variety of peach tree, characterized as to novelty by the flavor and juiciness of the fruit; low chilling requirement; size and shape of fruit; color of skin and flesh; shallow stem cavity and persistence of fruit to hang on tree; late ripening season and lack of tendency of the flesh to oxidize, substantially as shown and described.

LIDA BOYER,

*Administratrix of the Estate of John D. Davis, Deceased.*